United States Patent
Chen et al.

(10) Patent No.: US 9,483,819 B2
(45) Date of Patent: Nov. 1, 2016

(54) CONTOUR-BASED ARRAY INSPECTION OF PATTERNED DEFECTS

(71) Applicant: KLA-Tencor Corporation, Milpitas, CA (US)

(72) Inventors: Chien-Huei Chen, San Jose, CA (US); Ajay Gupta, San Jose, CA (US); Thanh Huy Ha, Milpitas, CA (US); Jianwei Wang, San Jose, CA (US); Hedong Yang, Santa Clara, CA (US); Christopher Michael Maher, Campbell, CA (US); Michael J. Van Riet, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 328 days.

(21) Appl. No.: 14/062,761

(22) Filed: Oct. 24, 2013

(65) Prior Publication Data

US 2014/0212024 A1    Jul. 31, 2014

Related U.S. Application Data

(60) Provisional application No. 61/757,807, filed on Jan. 29, 2013.

(51) Int. Cl.
  *G06T 7/00* (2006.01)
  *G01N 23/225* (2006.01)
  *H01L 21/66* (2006.01)

(52) U.S. Cl.
  CPC ........... *G06T 7/001* (2013.01); *G01N 23/2251* (2013.01); *G01N 2223/6116* (2013.01); *G06T 2207/10061* (2013.01); *G06T 2207/30148* (2013.01); *H01L 22/12* (2013.01)

(58) Field of Classification Search
  CPC ............... G01N 23/2251; G01N 2223/6116; G06T 7/001; G06T 2207/10061; G06T 2207/30148; H01L 22/12
  USPC .................................................. 382/141, 152
  See application file for complete search history.

(56) References Cited

U.S. PATENT DOCUMENTS

| 6,353,222 | B1 | 3/2002 | Dotan |
| 7,254,263 | B2 | 8/2007 | Ine |

(Continued)

FOREIGN PATENT DOCUMENTS

| JP | 2005309140 A | 11/2005 |
| JP | 2007255959 A | 10/2007 |

(Continued)

OTHER PUBLICATIONS

Yasutaka Toyoda, et al. "SEM-Contour Shape Analysis Method for Advanced Semiconductor Devices", Proc. of SPIE vol. 8681, 86811K • © 2013 SPIE, 10 pgs., Downloaded from: http://spiedigitallibrary.org/ on Dec. 3, 2013.

(Continued)

*Primary Examiner* — Edward Park
(74) *Attorney, Agent, or Firm* — Okamoto & Benedicto LLP (57) ABSTRACT

One embodiment relates to a method of inspecting an array of cells on a substrate. A reference image is generated using a cell image that was previously determined to be defect free. A reference contour image which includes contours of the reference image is also generated. The reference contour image is used to detect defects in the array of cells on the substrate. Another embodiment relates to a system for detecting defects in an array on a substrate. Other embodiments, aspects and features are also disclosed.

18 Claims, 8 Drawing Sheets

(56) References Cited

U.S. PATENT DOCUMENTS

| | | | |
|---|---|---|---|
| 7,475,383 B2 | 1/2009 | Suh et al. | |
| 7,869,643 B2 | 1/2011 | Litichever et al. | |
| 8,045,785 B2 | 10/2011 | Kitamura et al. | |
| 8,217,351 B2 | 7/2012 | Toyoda et al. | |
| 8,280,147 B2 | 10/2012 | Naoe et al. | |
| 8,285,031 B2 | 10/2012 | Kitamura et al. | |
| 8,515,155 B2 | 8/2013 | Toyoda et al. | |
| 2004/0052417 A1* | 3/2004 | Lee | G06T 7/001 382/199 |
| 2005/0157308 A1 | 7/2005 | Brunfeld et al. | |
| 2008/0130982 A1 | 6/2008 | Kitamura et al. | |
| 2009/0007052 A1 | 1/2009 | Yang | |
| 2009/0052765 A1 | 2/2009 | Toyoda et al. | |
| 2010/0310180 A1 | 12/2010 | Toyoda et al. | |
| 2011/0243424 A1 | 10/2011 | Wu et al. | |
| 2011/0276935 A1 | 11/2011 | Fouquet et al. | |
| 2012/0298862 A1 | 11/2012 | Chen et al. | |
| 2012/0300054 A1 | 11/2012 | Mito et al. | |
| 2013/0002849 A1 | 1/2013 | Sakai et al. | |
| 2013/0070078 A1* | 3/2013 | Takagi | G06T 7/001 348/80 |
| 2013/0119250 A1 | 5/2013 | Hosoya et al. | |
| 2013/0265408 A1* | 10/2013 | Yamaguchi | H01J 37/222 348/80 |
| 2013/0315468 A1 | 11/2013 | Toyoda et al. | |

FOREIGN PATENT DOCUMENTS

| | | |
|---|---|---|
| JP | 2011174858 A | 9/2011 |
| KR | 20090042456 A | 4/2009 |
| KR | 20090072670 A | 7/2009 |
| KR | 20100134452 A | 12/2010 |
| TW | 201300769 A | 1/2013 |
| WO | WO 2011/083540 A1 * | 7/2011 |
| WO | 2011/142196 A1 | 11/2011 |
| WO | 2012098605 A1 | 7/2012 |

OTHER PUBLICATIONS

Shaun S. Gleason, et al. "Detection of semiconductor defects using a novel fractal encoding algorithm", 11 pgs., publication/232644868_Detecting_Defects_in_Golden_Surfaces_of_Flexible_Printed_Circuits_Using_Optimal_Gabor_Filters, Dowloaded from: http://www.researchgate.net/.

I. Mochi, et al. "Actinic imaging of native and programmed defects on a full-field mask", Jul. 13, 2010, 9 pgs., Dowloaded from: http://escholarship.org/.

Qingxiang Wang, et al. "Detecting Defects in Golden Surfaces of Flexible Printed Circuits Using Optimal Gabor Filters", 3 pgs., Intelligent Information Technology Applications, 2007 Workshop on Jan. 2008, Dowloaded from: http://www.researchgate.net/.

International Search Report and Written Opinion of the International Searching Authority for PCT Application No. PCT/US2014/013675, May 26, 2014, 8 sheets.

Virginia Brecher, et al "The P300: An Approach to Automated Inspection of Patterned Wafers", Feb. 27, 1989, pp. 200-206, SPIE vol. 1087 Integrated Circuit Metrology, Inspection and Process Control III.

The extended European Search Report for Application No. 14 745 726.1, dated Aug. 31, 2016 [Aug. 31, 2016], 8 sheets.

* cited by examiner

FIG. 3    Golden Cell Setup and Definition    300

FIG. 4     Pitch computation 400

FIG. 6  High-resolution golden cell image acquisition
600

FIG. 7 Golden cell contour extraction and context ROI definition
700

FIG. 8

FIG. 9  Golden cell contour-based defect detection
900

CONTOUR-BASED ARRAY INSPECTION OF PATTERNED DEFECTS

CROSS-REFERENCE TO RELATED APPLICATION(S)

The present application claims the benefit of U.S. provisional patent application No. 61/757,807, filed Jan. 29, 2013, entitled "Ebeam Array Inspection (Detection and Classification) of Patterned Defects in Semiconductor Wafers Using Golden Cell Contours," the disclosure of which is hereby incorporated by reference in its entirety.

BACKGROUND OF THE INVENTION

1. Field of the Invention

The present invention relates to inspection and review of substrates, such as, for example, semiconductor wafers and reticles for lithography.

2. Description of the Background Art

In a conventional electron beam (e-beam) inspection instrument, a manufactured substrate (such as a silicon wafer or a reticle) is scanned with a focused beam of electrons which results in the emission of secondary electrons from the substrate surface. The emitted electrons are detected, and the detection data is typically converted into images of the surface of the specimen. These images are then analyzed numerically to detect abnormalities (referred to as defects) in the manufactured substrate. The detected defects may be subsequently reviewed by further imaging.

The detected defects may also be classified, either manually or automatically, into different classes or categories. The classification of a defect may be used to determine its cause such that appropriate adjustments may be made in the manufacturing process so as to improve its yield.

It is highly desirable to improve methods and apparatus for the detection and classification of defects imaged by electron beam instrumentation.

SUMMARY

One embodiment relates to a method of inspecting an array of cells on a substrate. A reference image is generated using a cell image that was previously determined to be defect free. A reference contour image which includes contours of the reference image is also generated. The reference contour image is used to detect defects in the array of cells on the substrate.

Another embodiment relates to a system for detecting defects in an array on a substrate. A source generates an incident electron beam, and a scanning system for controllably deflecting the incident electron beam to scan the incident electron beam over a target region on the substrate such that secondary electrons are emitted therefrom. A detection system detects the secondary electrons and generates an image data frame of the target region. A control and processing system with control code is programmed to generate a reference image using a cell image that was previously determined to be defect free, generate a reference contour image which includes contours of the reference image, and use the reference contour image to detect defects in the array of cells on the substrate.

Other embodiments, aspects and features are also disclosed.

DETAILED DESCRIPTION

A conventional method of defect detection in an array region of a wafer relies on cell-to-cell (C2C) comparison or cell-to-reference-cell comparison (see, for example, U.S. Pat. No. 7,869,643). However, in electron beam (ebeam) inspection, it is possible to have very small pixel sizes which causes an insufficient number of cells to be available in a given frame to perform cell-to-cell comparison.

In such cases, the user will generally be forced to inspect the array region using cells in adjacent dies as reference cells or previously-determined defect-free cell images (so-called "golden" cell images) for the reference cells. In the former case, there is a disadvantageous loss of sensitivity and throughput due to the need to use cells in adjacent dies. In the latter case, there is a disadvantageous loss of sensitivity since the golden (previously-determined defect-free) cell images may have been obtained with very different image quality in comparison to the test image.

Even if there is a sufficient number of cells in a given frame to perform C2C comparison, the sensitivity of using another cell in the frame (or a golden cell) for the C2C comparison may be somewhat limited and may be improved by the use of methods and apparatus using "golden" cell contours as disclosed herein.

Methods and apparatus for contour-based defect detection and classification using an e-beam apparatus are disclosed herein. These methods and apparatus may be employed to substantially improve the sensitivity of defect detection when compared against a conventional approaches.

In particular, array defect detection using golden cell contours as disclosed herein has higher sensitivity than previous approaches, such as using an adjacent cell or a golden cell as a reference. The previous approaches also have a higher noise floor due to process variation across cells or dies. However, the contour-based defect detection technique disclosed herein uses contour-based segmentation and local differencing to substantially reduce the noise floor and thereby substantially enhance sensitivity.

Figure 1:
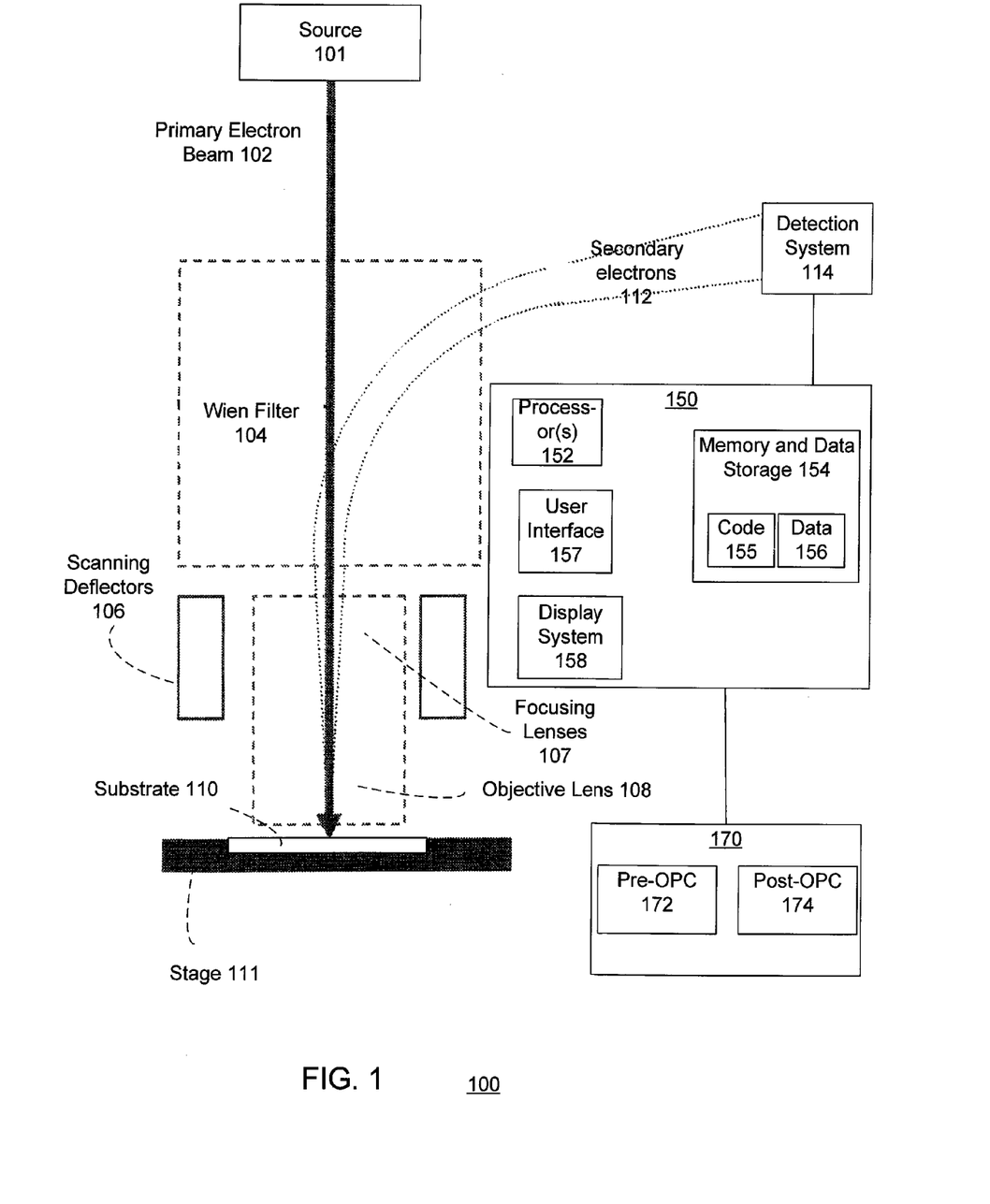
FIG. 1 is a schematic diagram of an e-beam apparatus in accordance with an embodiment of the invention.

FIG. 1 provides a cross-sectional diagram of the e-beam inspection apparatus 100 which may be utilized in accordance with an embodiment of the invention. As shown in FIG. 1, a source 101 generates an incident electron beam (primary electron beam) 102. The incident electron beam 102 passes through a Wien filter 104. The Wien filter 104 is an optical element configured to generate electrical and magnetic fields which cross each other. Scanning deflectors 106 and focusing electron lenses 107 are utilized. The scanning deflectors 106 are utilized to scan the e-beam across the surface of the target substrate 110. The target substrate 110 may be, for example, a patterned substrate, such as an integrated circuit being manufactured or a reticle for lithography.

The focusing electron lenses 107 are utilized to focus the incident electron beam 102 into a beam spot on the surface of the wafer or other substrate sample 110. In accordance with one embodiment, the focusing lenses 107 may operate by generating electric and/or magnetic fields.

As a result of the scanning of the incident electron beam 102, secondary electrons are emitted or scattered from the surface of the target substrate 110 (which may be, for example, a semiconductor wafer or a reticle). The target substrate 110 may be held by a movable stage 111. The secondary electrons are then extracted from the target substrate 110 by exposure to the electromagnetic field of the objective (final) lens 108. The electromagnetic field acts to confine the emitted electrons to within a relatively small distance from the incident electron beam optic axis and to accelerate these electrons up into the column. In this way, a secondary e-beam 112 is formed from the secondary electrons.

The Wien filter 104 deflects the secondary e-beam 112 from the optic axis of the incident electron beam 102 to a detection axis (the optic axis for the detection system 114 of the apparatus). This serves to separate the scattered e-beam 112 from the incident electron beam 102. The detection system 114 detects the secondary e-beam 112 and generates data signals that may be utilized to create images of the surface of the target substrate.

An instrument control and data processing (control/processing) system 150 may include one or more processors (i.e. microprocessors or microcontrollers) 152, data storage (including, for example, hard disk drive storage and memory chips) 154, a user interface 157 and a display system 158. The data storage 154 may store or hold computer-readable program code (instructions) 155 and data 156, and the processor 152 may execute the program code 155 and process the data 156. The user interface 157 may receive user inputs. The display system 158 may be configured to display image data and other information to a user.

The control/processing system 150 may be connected to, and may be used to control, various components of the e-beam column so as to implement methods or procedures disclosed herein. For example, the movement of the stage 111, and the scanning by the deflectors 106 may be controlled by computer-readable program code 155 executed by the control/processing system 150.

In addition, the control/processing system 150 may also process the electron image data from the detection system 114. In particular, the computer-readable program code 155 in the control/processing system 150 may be used to implement procedures relating to the contour-based array inspection of patterned defects as described herein.

Furthermore, in accordance with an embodiment of the invention, the control/processing system 150 may, optionally, interface with a design server 170. The design server 170 may store pre-OPC (optical proximity correction) design patterns 172 and post-OPC design patterns 174. During an inspection run, the design server 170 may provide said data in design clips in real-time at the request of the control/processing system 150 of the e-beam inspection apparatus 100.

For embodiments where no design server is available, a image editing tool may be used by the user to manually draw the golden contours (i.e. contours in the previously-determined defect-free images). The image editing tool may display an input SEM image to guide the user in drawing the golden contours.

Figure 2:
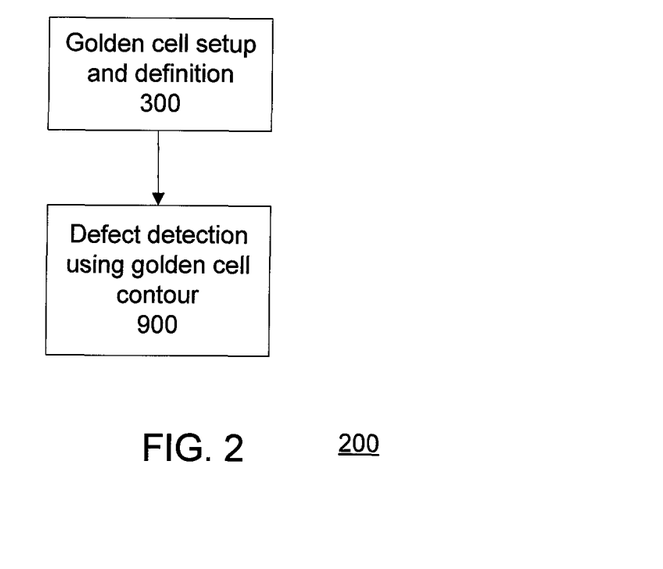
FIG. 2 is a flow diagram of a method for array defect detection and classification in accordance with an embodiment of the invention.

FIG. 2 is a flow diagram of a method 200 for array defect detection and classification in accordance with an embodiment of the invention. As shown, the method 200 may include a golden cell set-up and definition procedure 300 and a procedure 900 for defect detection using a golden cell contour. Both of these procedures are described further below.

Note that various modes of inspection may be provided by the system, including array and non-array modes. In one implementation, a user may select an array mode of inspection. In addition, under the array mode, multiple detection techniques may be provided by the system. A user may select a contour-based detection technique. Furthermore, under the contour-based technique, multiple types of reference cells may be used. In accordance with an embodiment of the invention, a user may specify the reference type as a "golden cell" (i.e. a known defect-free cell).

Figure 3:
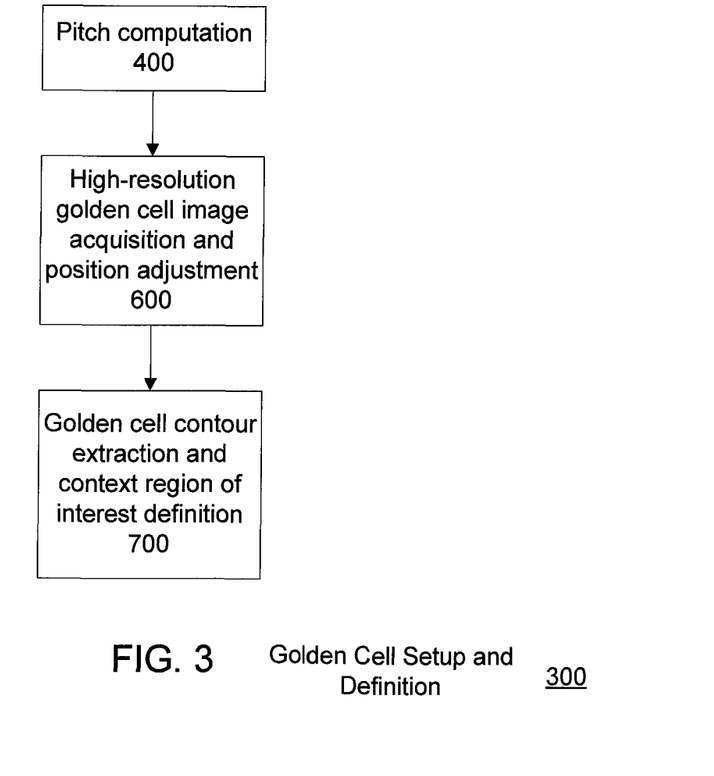
FIG. 3 is a flow diagram of a golden cell set-up and definition procedure in accordance with an embodiment of the invention.

FIG. 3 is a flow diagram of a golden cell set-up and definition procedure 300 in accordance with an embodiment of the invention. User input steps in this procedure (and elsewhere in this specification) may be implemented using a display screen and user interface (such as a mouse, touchscreen or trackball, for example).

As shown, a pitch computation procedure 400 may be performed. An exemplary pitch computation procedure 400 is described below in relation to FIG. 4.

Next, a procedure 600 for high-resolution golden cell image acquisition and position adjustment may be performed. An exemplary such procedure 600 is described below in relation to FIG. 6.

Subsequently, a golden cell contour extraction and context region of interest (ROI) definition procedure 700 may be performed. An exemplary such procedure 700 is described below in relation to FIG. 7.

Figure 4:
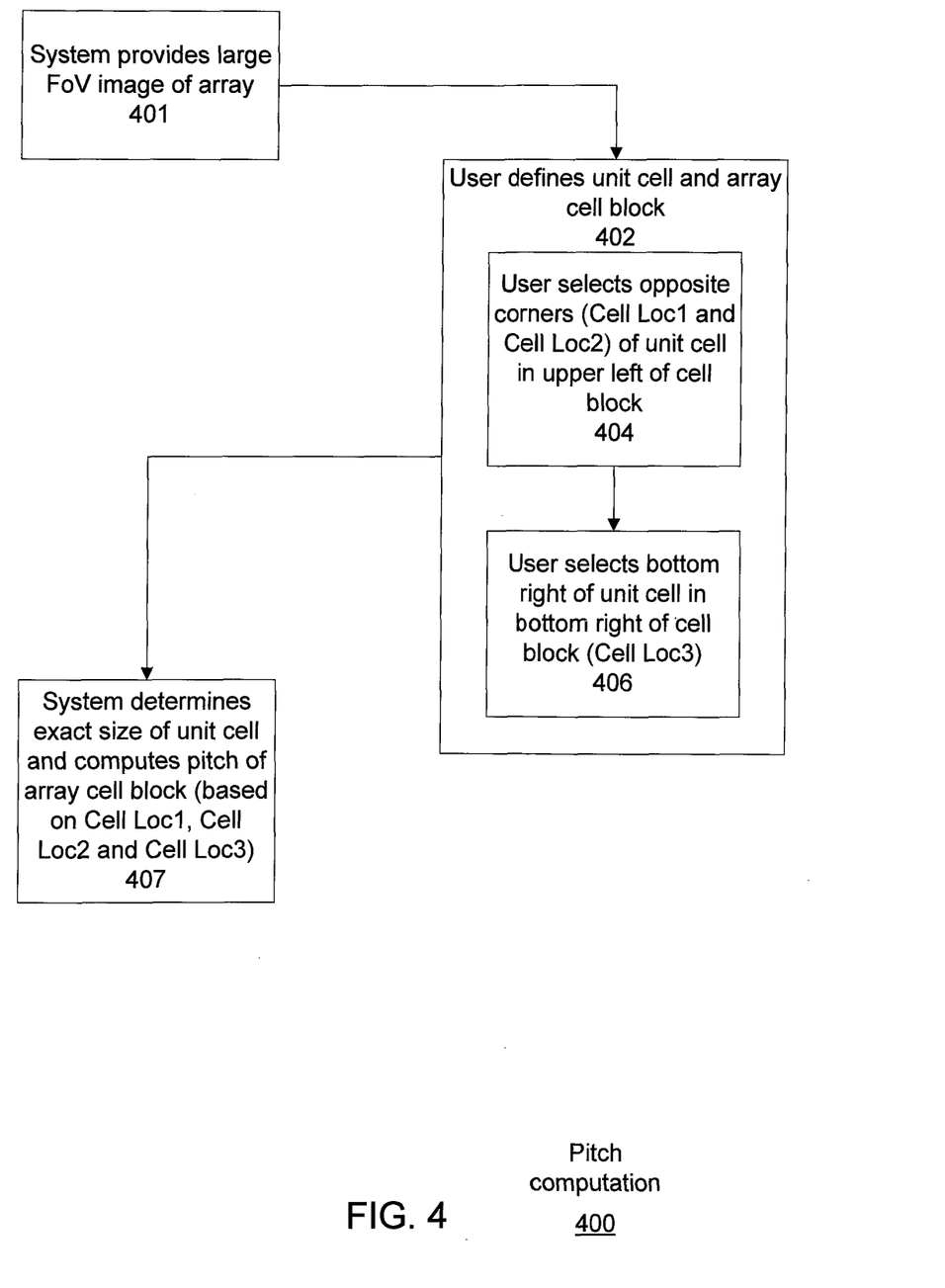
FIG. 4 is a flow diagram of an exemplary pitch computation procedure in accordance with an embodiment of the invention.

FIG. 4 is a flow diagram of an exemplary pitch computation procedure 400 in accordance with an embodiment of the invention. In the method 200 of FIG. 2, this procedure 400 may be performed as part of the golden cell set-up and definition procedure 300 of FIG. 3. User input steps in this procedure may be implemented using a display screen and user interface (such as a mouse, touchscreen or trackball, for example).

In step 401, the system may provide a large field of view (FoV) image of the array. The large FoV image shall be longer than one cell in each dimension.

In step 402, the user defines a unit cell and an array cell block within the large FoV image. The array cell block may be two-dimensional (with multiple cells arranged in a two-dimensional array) or one-dimensional (with multiple cells arranged in a one-dimensional array). In one implementation, step 402 may be implemented with steps 404 and 406.

Per step 404, the user may select the top left (Cell Loc1) and bottom right (Cell Loc2) (i.e. opposite corners) of a unit cell at one corner of the array cell block. In one implementation, the defined unit cell may be the cell in the upper left corner of the array cell block. Per step 406, the user may select the bottom right (Cell Loc3) of the array cell block (i.e. the bottom right of the cell in the bottom right of the array cell block).

In step 407, the system may determine exact size of the unit cell and compute the pitch in each dimension of the array cell block. This determination may be based on the user inputs for Cell Loc1, Cell Loc2, and Cell Loc3.

Figure 5A:
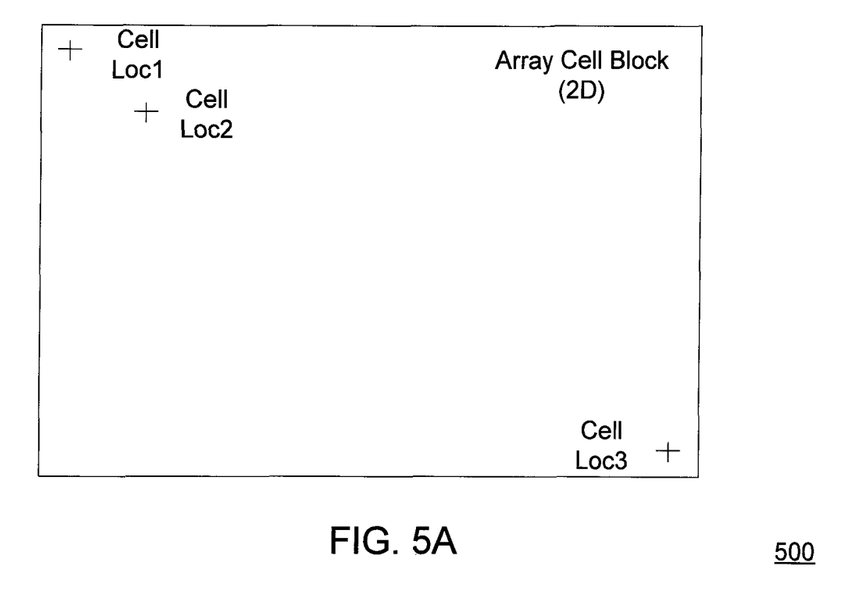
FIG. 5A depicts example cell location selections for a two-dimensional cell array in accordance with an embodiment of the invention.

FIG. 5A depicts example cell location selections for a two-dimensional cell array in accordance with an embodiment of the invention. As shown, Cell Loc1 and Cell Loc 2 define the opposite corners of a unit cell in the upper left of the array cell block. Cell Loc 3 defines the bottom right corner of the cell in the bottom right of the array cell block. From Cell Loc 1, Cell Loc 2, and Cell Loc 3, the horizontal and vertical pitches may be computed for the cells in the two-dimensional cell array.

Figure 5B:
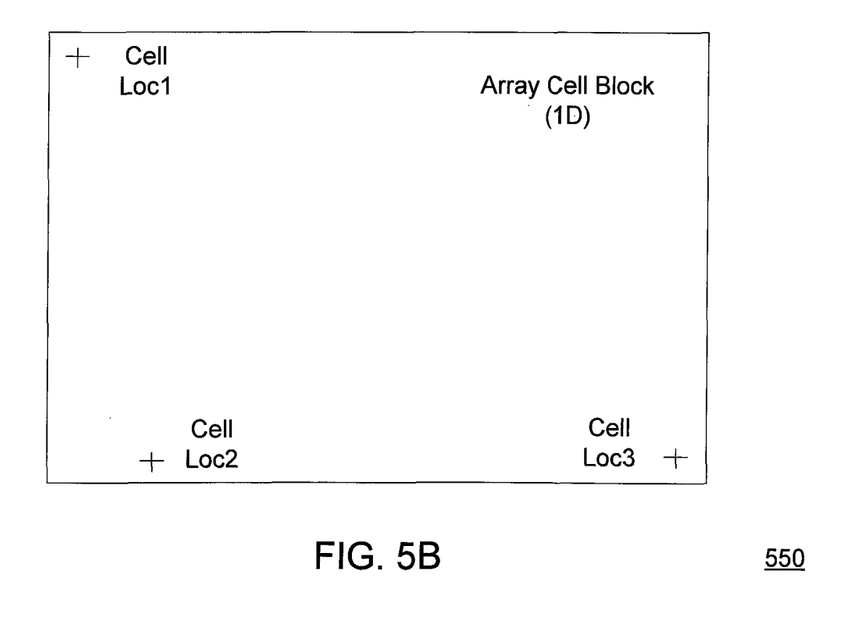
FIG. 5B depicts example cell location selections for a one-dimensional cell array in accordance with an embodiment of the invention.

FIG. 5B depicts example cell location selections for a one-dimensional cell array in accordance with an embodiment of the invention. As shown, Cell Loc1 and Cell Loc 2 define the opposite corners of a unit cell at the left of the array cell block. Cell Loc 3 defines the bottom right corner of the cell at the right of the array cell block. From Cell Loc 1, Cell Loc 2, and Cell Loc 3, the horizontal pitch may be computed for the cells in the one-dimensional cell array.

Figure 6:
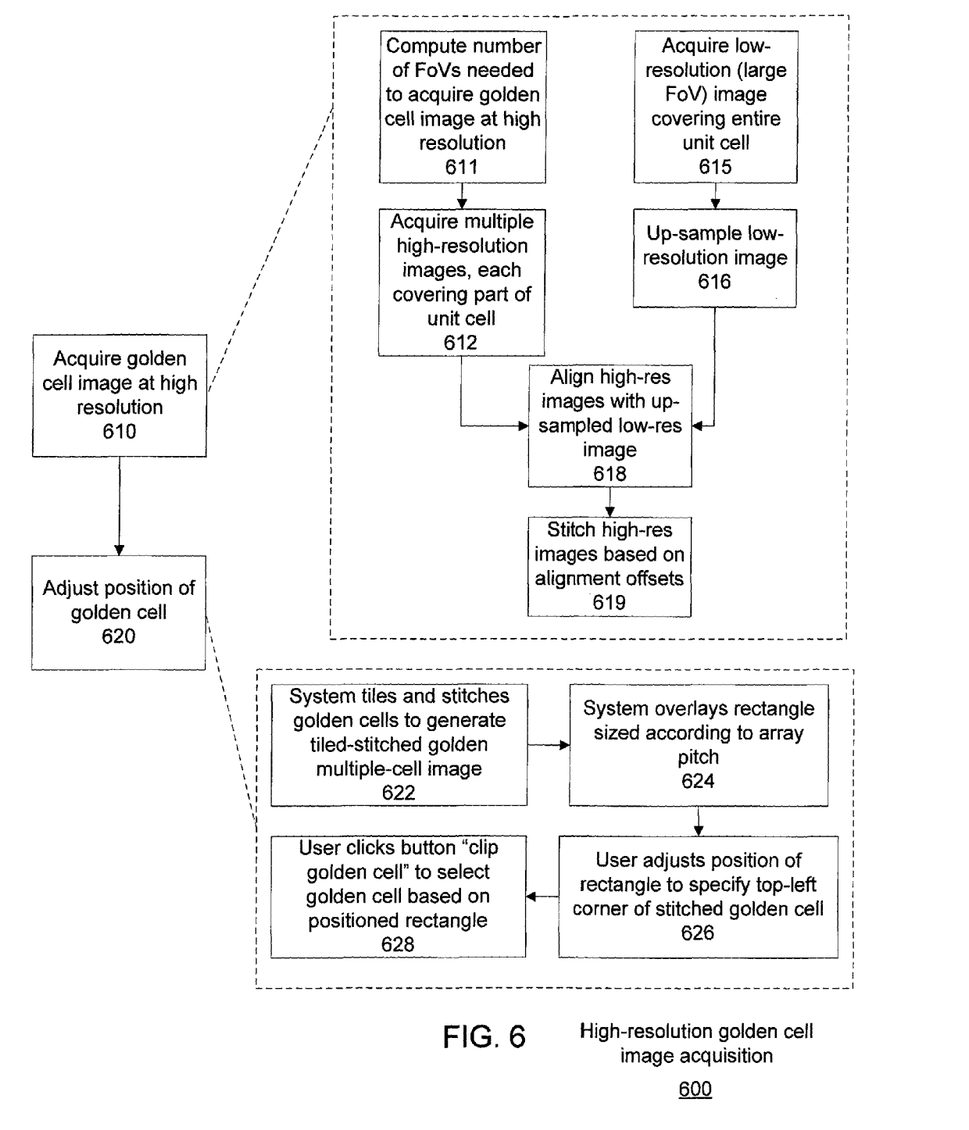
FIG. 6 is a flow diagram of an exemplary procedure for high-resolution golden cell image acquisition and position adjustment in accordance with an embodiment of the invention.

FIG. 6 is a flow diagram of a procedure 600 for high-resolution golden cell image acquisition and position adjustment in accordance with an embodiment of the invention. In the method 300 of FIG. 3, this procedure 600 may be performed after the pitch computation procedure 400 of FIG. 4. User input steps in this procedure may be implemented using a display screen and user interface (such as a mouse, touchscreen or trackball, for example).

Per block 610, the system may acquire a golden (i.e. previously-determined to be defect-free or "known good") cell image at high resolution. As shown, the golden cell image acquisition may include several steps in an exemplary implementation. In step 611, the system may compute the number of field of views (FoVs) needed to acquire the golden cell image at a high resolution setting of the system. The computation of the number of FoVs may be based on the cell size, the positional uncertainty due to the stage, and the FoV (or pixel size). In step 612, the multiple FoVs are acquired, each FoV covering part of the unit cell and overlapping adjacent FoVs. In addition, a lower-resolution (i.e. larger FoV) image covering the entire unit cell may be acquired per step 615, and the low-resolution image may be up-sampled per step 616. The up-sampling increases a number of pixels in the image so that the lower-resolution image may be compared pixel for pixel against the high-resolution images acquired in step 612. Per block 618, the high-resolution images may be aligned using the up-sampled lower resolution image as a guide to determine the alignment offsets. The high-resolution images may then be stitched based on the alignment offsets to generate the golden cell image at high resolution.

Per block 620, the system may adjust a position of the golden cell image. As shown, the position adjustment may be performed using several steps in an exemplary implementation. In a first step 622, the system may tile and stitch golden cells to generate a tiled-stitched golden multiple-cell image. This step may be performed by tiling copies of the high-resolution golden cell image and stitching together the tiled copies to create the tiled-stitched golden multiple-cell image. In other words, the high-resolution golden cell image is replicated and then stitched to create a high-resolution multiple-cell image. Subsequently, in a second step 624, the system may overlay a rectangle over the tiled-stitched golden multiple-cell image. The rectangle may be sized according to the array pitch(es) previously determined. In a third step 626, the user may then adjust the position of the rectangle to specify a corner (for example, the top-left corner) of a single stitched golden cell within the tiled-stitched golden multiple-cell image. Finally, in a fourth step 628, the user may click on a button labeled "clip golden cell" to select a single golden cell based on the user-positioned rectangle. In other words, a smaller frame of pixels encompassing a single golden cell is selected at the desired position is obtained.

Figure 7:
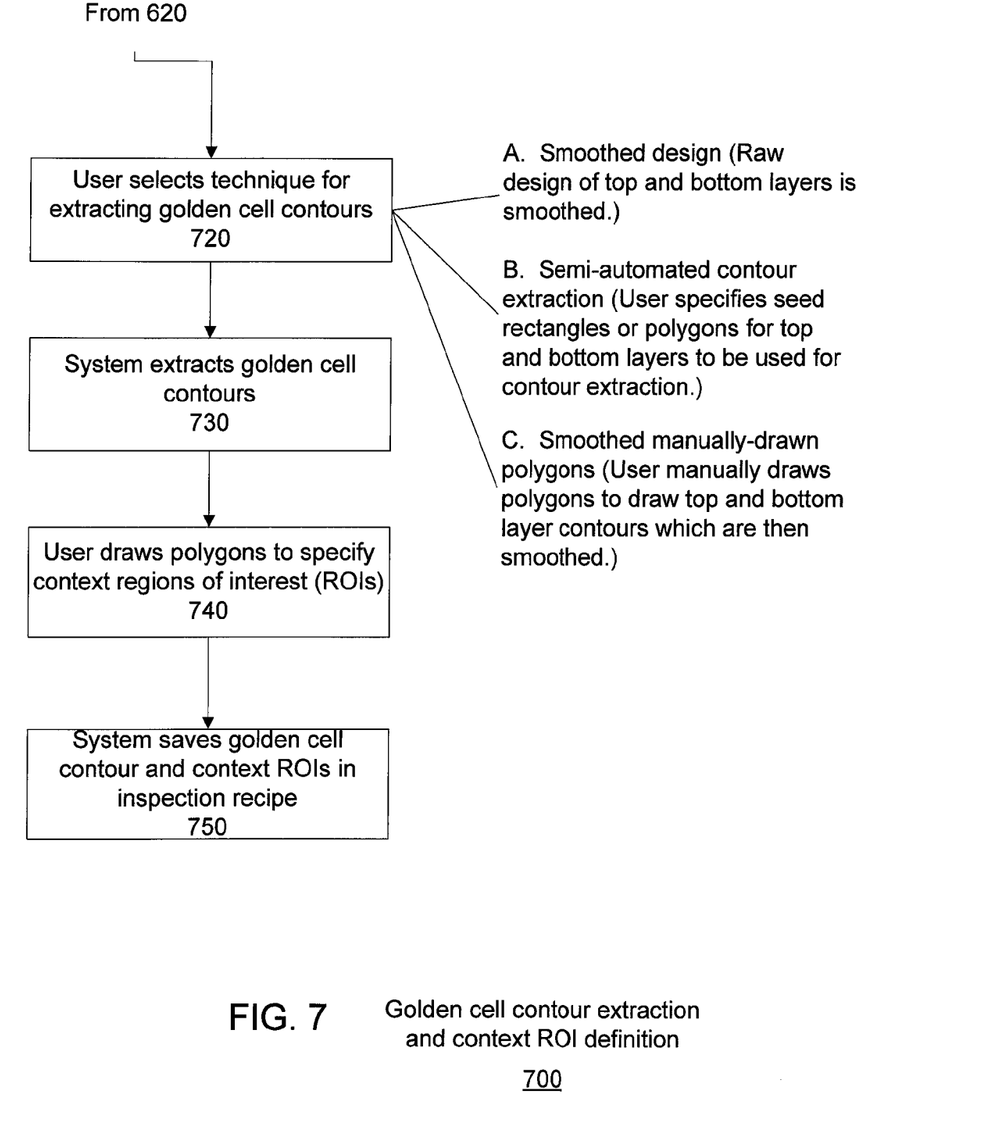
FIG. 7 is a flow diagram of an exemplary procedure for golden cell contour extraction and context ROI definition in accordance with an embodiment of the invention.

FIG. 7 is a flow diagram of a procedure 700 for golden cell contour extraction and context ROI definition in accordance with an embodiment of the invention. This procedure 700 may be performed after the procedure 600 of FIG. 6. User input steps in this procedure may be implemented using a display screen and user interface (such as a mouse, touchscreen or trackball, for example).

Per block 720 (which may be performed after block 620 of FIG. 6), the user may select a technique for extracting golden cell contours from the selected golden cell. As indicated, multiple technique options may be provided, such as: A) a smoothed design technique; B) a semi-automated contour extraction technique; and C) a smoothed manually-drawn polygons technique. The smoothed design technique may involve smoothing pre-OPC design data of the top and bottom layers. The semi-automated contour extraction technique may be a watershed technique. The semi-automated contour extraction technique may involve a user specifying seed rectangles or polygons for top and bottom layers to be used for the contour extraction. In one implementation, polygons of the design may be used as the seeds for extracting the contours. The smoothed manually-drawn polygons technique may involve a user manually drawing polygons using an image editing tool to create top and bottom layer contours which may then be smoothed.

Per block 730, the system may then extract golden cell contours using the selected technique. A contour may be defined and stored as a list of points or locations. The golden cell contours may then be overlaid on top of the golden cell image in the display to the user.

Per block 740, the user may then draw polygons to specify context regions of interest (ROIs). The context ROIs are to be used for subsequent binning and nuisance filtering.

Per block 750, the system may save the golden cell contour and context ROIs in an inspection recipe. The inspection recipe may be subsequently used to inspect an area of a substrate with the patterned array of cells. The golden cell contour and/or context ROIs may be used, for example, to create a mask image to provide user-specified segmentation for defect detection, nuisance filtering, and binning and/or classification.

Figure 8:
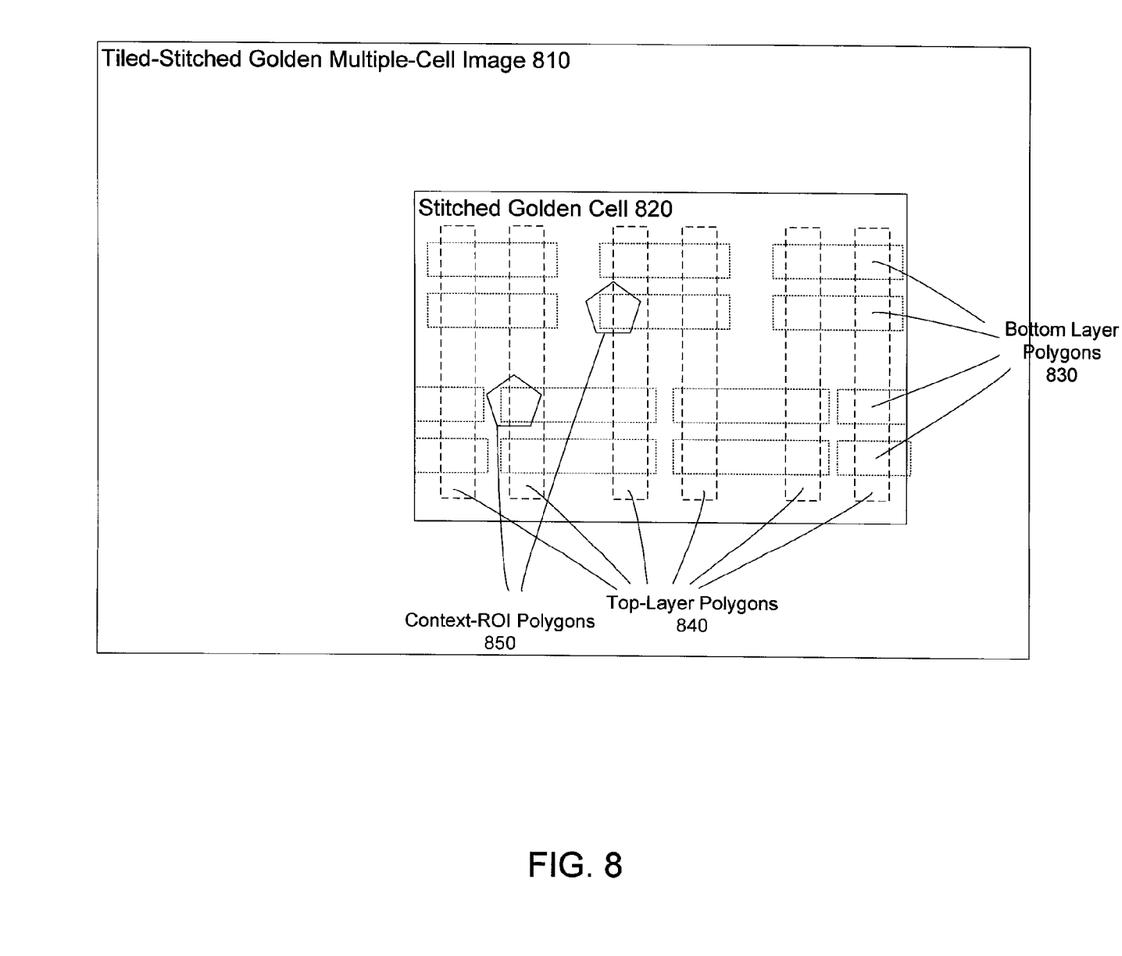
FIG. 8 depicts example previous-layer, top-layer and context ROI polygons within a stitched golden cell in accordance with an embodiment of the invention.

FIG. 8 depicts example bottom-layer, top-layer and context ROI polygons within a stitched golden cell in accordance with an embodiment of the invention. Shown in FIG. 8 is an outline of a tiled-stitched golden multiple-cell image, and a selected stitched golden cell 820 therein. Also depicted are bottom layer (i.e. previous layer) polygons 830 and top layer (i.e. subsequent layer) polygons 840. In addition, example context ROI polygons 850 are depicted.

Figure 9:
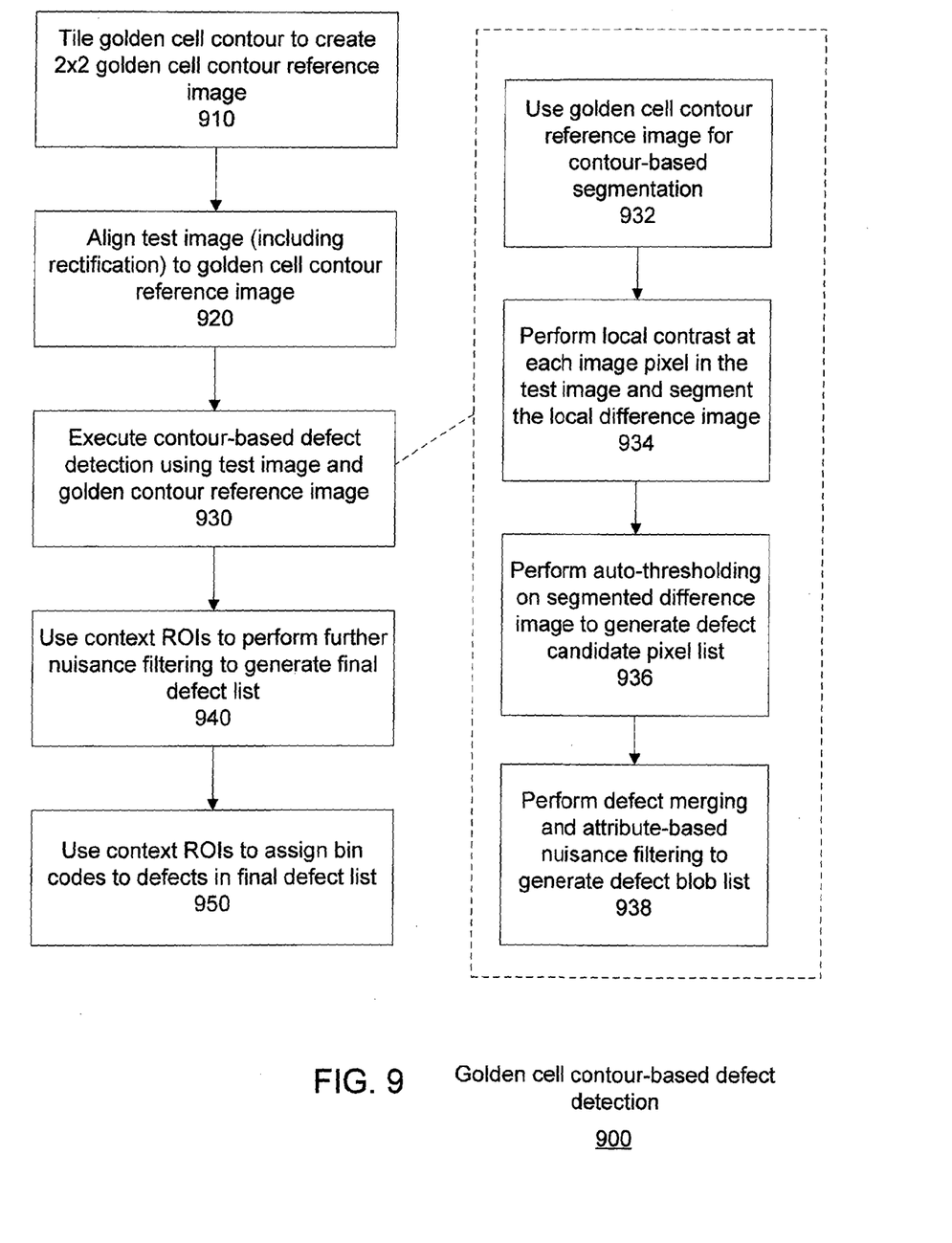
FIG. 9 is a flow diagram of an exemplary procedure for automated defect detection using golden cell contours in accordance with an embodiment of the invention.

FIG. 9 is a flow diagram of a procedure 900 for automated defect detection (i.e. automated inspection) using golden cell contours in accordance with an embodiment of the invention. This procedure 900 may be performed after the procedure 300 of FIG. 3.

Per block 910, the extracted golden cell contour may be tiled to create a corresponding 2×2 tiled golden cell contour reference image. Preferably, some additional margin is added to create a reference image that is slightly larger than 2×2 cells so as to account for stage uncertainty.

Per block 920, a test image may then be rectified and aligned to the golden cell contour reference image. The test image is an image of an area to be inspected for defects by comparison against the golden cell contour reference image.

Per block 930, a contour-based defect detection procedure may be executed using the test image and the golden cell contour reference image. As depicted in FIG. 9, this procedure may involve several steps. In a first step 932, contour-based segmentation may be performed based on the contours of the golden cell contour reference image. In other words, the test image may be segmented or separated into regions based on the contours of the golden cell contour reference image. In one implementation, corners and/or contours at various distances from the edges of the golden cell contours may be segmented out to improve defect detection sensitivity. In a second step 934, local contrast may be performed at each image pixel in the test image. The local difference image may then be segmented into image regions (or image segments) using the contour-based segmentation. In a third step 936, auto-thresholding may be performed on the segmented difference image to generate a defect candidate pixel list. In a fourth step 938, defect merging (i.e. merging of candidate defect pixels) and attribute-based nuisance filtering may be performed to generate a defect blob list.

Per block 940, the context ROIs may be used to perform further nuisance filtering to generate a final defect list. Per block 950, the context ROIs are used to assign bin codes to defects in the final defect list.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of inspecting an array of cells on a substrate, the method comprising:
    obtaining a first cell image that was previously determined to be defect free;
    generating an array image by tiling and stitching copies of the first cell image;
    generating a reference image by defining a second cell image within the array image and tiling and stitching copies of the second cell image;
    generating a reference contour image which includes contours extracted from the reference image; and
    using the reference contour image to detect defects in the array of cells on the substrate.

2. The method of claim 1 further comprising:
    acquiring a test image of the array of cells on the substrate; and
    aligning the test image to the reference contour image.

3. The method of claim 1 further comprising:
    acquiring multiple overlapping higher-resolution partial images of a cell;
    acquiring a lower-resolution full image of the cell; and
    aligning and stitching the partial images to obtain the first cell image.

4. The method of claim 1 further comprising:
    generating a cell contour image from the second cell image; and
    generating the reference contour image by tiling copies of the cell contour image.

5. The method of claim 4, wherein generating the cell contour image comprises extracting cell contours using a watershed technique.

6. The method of claim 4, wherein generating the cell contour image comprises using polygons of the design as seeds for extracting cell contours.

7. The method of claim 4, wherein generating the cell contour image comprises obtaining cell contours by smoothing a pre-optical-proximity-correction design.

8. The method of claim 4, wherein generating the cell contour image comprises manually drawing cell contours using an image editing tool.

9. The method of claim 1 further comprising:
    creating a mask image to provide user-specified segmentation for defect detection.

10. The method of claim 9, wherein features are segmented out depending on a distance from edges of cell contours.

11. The method of claim 9, wherein the user-specified segmentation is further used for defect classification.

12. A system for detecting defects in an array on a substrate, the system comprising:
    a control and processing system comprising a microprocessor and control code programmed to
        generate a reference image by obtaining a first cell image that was previously determined to be defect free, generating an array image by tiling and stitching copies of the first cell image, defining a second cell image within the array image, and generating a reference image by tiling and stitching copies of the second cell image,
        generate a reference contour image which includes contours of extracted from the reference image, and
        use the reference contour image to detect defects in the array of cells on the substrate.

13. The system of claim 12, wherein the control code is further programmed to
    acquire a test image of the array of cells on the substrate, and
    align the test image to the reference contour image.

14. The system of claim 12, wherein the control code is further programmed to
    acquire multiple overlapping higher-resolution partial images of a cell,
    acquire a lower-resolution full image of the cell, and align and stitch the partial images to obtain the first cell image.

15. The system of claim 12, wherein the control code is further programmed to generate a cell contour image from the second cell image; and generate the reference contour image by tiling copies of the cell contour image.

16. The system of claim 12, wherein the control code is further programmed to create a mask image to provide user-specified segmentation for defect detection.

17. The system of claim 16, wherein features are segmented out depending on a distance from edges of cell contours.

18. The system of claim 16, wherein the user-specified segmentation is further used for defect classification.

* * * * *